(12) United States Patent
Chin

(10) Patent No.: US 9,420,798 B2
(45) Date of Patent: Aug. 23, 2016

(54) PREPARATION OF SILVER ION

(76) Inventor: Raymond Chin, Hong Kong (CN)

( * ) Notice: Subject to any disclaimer, the term of this patent is extended or adjusted under 35 U.S.C. 154(b) by 170 days.

(21) Appl. No.: 13/508,123

(22) PCT Filed: Nov. 6, 2009

(86) PCT No.: PCT/CN2009/074848
§ 371 (c)(1),
(2), (4) Date: Jul. 24, 2012

(87) PCT Pub. No.: WO2011/054153
PCT Pub. Date: May 12, 2011

(65) Prior Publication Data
US 2012/0282347 A1 Nov. 8, 2012
US 2013/0045281 A2 Feb. 21, 2013

(51) Int. Cl.
*C22B 11/00* (2006.01)
*A01N 59/16* (2006.01)
*A01P 1/00* (2006.01)
*B05D 3/00* (2006.01)

(52) U.S. Cl.
CPC ........ *A01N 59/16* (2013.01); *Y10T 428/12063* (2015.01)

(58) Field of Classification Search
None
See application file for complete search history.

(56) References Cited

U.S. PATENT DOCUMENTS

| 5,788,738 A * | 8/1998 | Pirzada et al. .................. 75/331 |
| 2001/0009689 A1 * | 7/2001 | Himeshima et al. ........... 427/64 |
| 2005/0008861 A1 * | 1/2005 | Yadav et al. .................. 428/403 |
| 2005/0034668 A1 * | 2/2005 | Garvey et al. ............ 118/723 R |

FOREIGN PATENT DOCUMENTS

| CN | 1149039 A | | 5/1997 |
| CN | 1934954 A | | 3/2007 |
| CN | 101263826 A | * | 9/2008 |
| EP | 0860516 A2 | * | 8/1998 |
| WO | 2006/004297 A1 | | 1/2006 |

OTHER PUBLICATIONS

Ionic Radius, Wikipedia, 2013, p. 5, obtained from http://en.wikipedia.org/wiki/Ionic_radius.*
Gandhi, Acta Materialia, 50, 2002.*
Silver, Melting and Boiling Temperatures, Engineering Toolbox, 2013 obtained from http://www.engineeringtoolbox.com/melting-boiling-temperatures-d_392.html.*
International Search Report mailed Aug. 19, 2010 issued in International Patent Application No. PCT/CN2009/074848 (with translation).

* cited by examiner

*Primary Examiner* — Susan Tran
*Assistant Examiner* — William Craigo
(74) *Attorney, Agent, or Firm* — Ping Wang; Andrews Kurth LLP

(57) ABSTRACT

Disclosed is a process for preparing silver ions ($Ag^+$) comprising treating element metal silver ($Ag^0$) under high temperature and high pressure, and quickly cooling to directly obtain the silver ions ($Ag^+$).

6 Claims, 3 Drawing Sheets

PREPARATION OF SILVER ION

FIELD

The present application is generally directed to silver ions preparing. The present application is also directed to silver ions, a surface coated with the silver ions, a process for preparing an antimicrobial surface and a process for inhibiting microbes.

BACKGROUND

Nowadays, all the processes for preparing silver ions in the art are focusing on the reactions carried out between metal oxides and element silver ($Ag^0$). For example, titanium dioxide is mixed with element silver ($Ag^0$) in a polymeric resin sol of particulate inorganic silicates, and the element silver is oxidized to silver ions ($Ag^+$) by heating and chemical reaction or by electrochemistry reaction.

However, the processes for preparing silver ions in the art have several disadvantages.

(1) As silver ions ($Ag^+$) are prepared in a solution, the preparation process is quite complicated and the cost is higher.

(2) The process for coating the resultant silver ions ($Ag^+$) on relevant products is complicated. The preparation time is long. The resultant products have low plasticity. Therefore, it is difficult to carry out a mass production at low cost, or meet the needs for substrates having different materials, different sizes and different shapes in the instant market.

SUMMARY

It is intended to resolve one of the disadvantages in the art by the present application. Therefore, the present application provides a process for preparing silver ions, silver ions prepared with the process, an antimicrobial surface coated with the silver ions prepared with the process, and a process for inhibiting microbes.

Therefore, in one aspect, the present application is directed to a process for preparing silver ions ($Ag^+$), comprising treating element metal silver ($Ag^0$) under high temperature and high pressure, and quickly cooling to directly obtain the silver ions ($Ag^+$).

In another aspect, the present application is also directed to silver ions (Ag+), wherein the silver ions ($Ag^+$) are directly obtained by treating element metal silver) ($Ag^0$) under high temperature and high pressure treatment and quickly cooling.

In another aspect, the present application is also directed to a surface coated with silver ions ($Ag^+$) directly obtained by treating element metal silver ($Ag^0$) under high temperature and high pressure treatment and quickly cooling.

In another aspect, the present application is also directed to a process for preparing an antimicrobial surface, comprising coating silver ions ($Ag^+$) prepared by treating element metal silver ($Ag^0$) under high temperature and high pressure and quickly cooling on a surface to obtain the antimicrobial surface.

In other aspect, the present application is also directed to a process for inhibiting microbes, comprising applying silver ions ($Ag^+$) directly obtained by treating element metal silver ($Ag^0$) under high temperature and high pressure and quickly cooling, to a product in need of antimicrobial effects.

DETAILED DESCRIPTION

Figure 1:
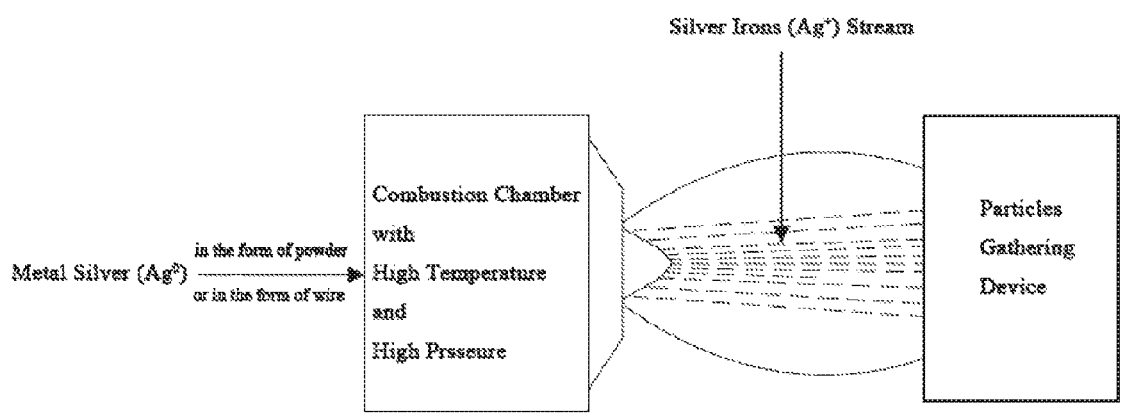
FIG. 1 is a schematic diagram of the silver ions preparing and recovering of the present application.
Figure 2:
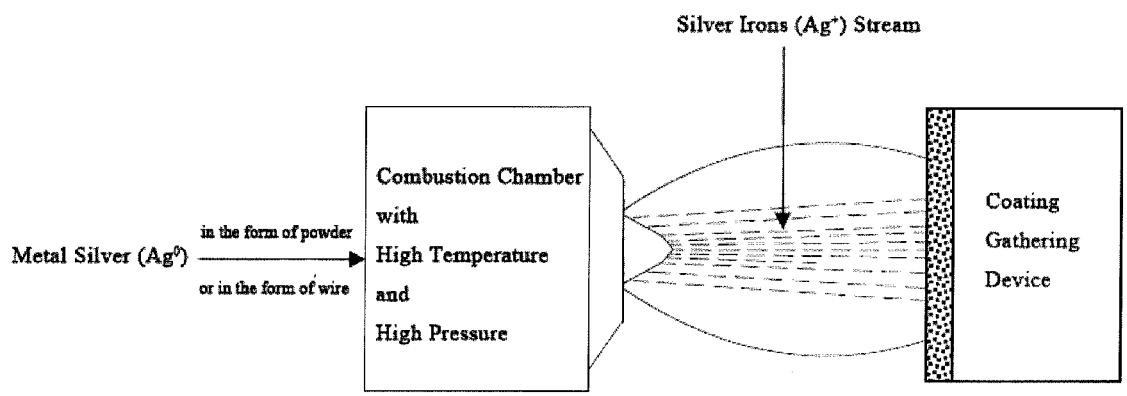
FIG. 2 is a schematic diagram of the silver ions preparing and the silver ions coating preparing of the present application.

In the following description, certain specific details are included to provide a thorough understanding of various disclosed embodiments. One skilled in the relevant art, however, will recognize that the embodiments may be practiced without one or more of these specific details, or with other methods, components, materials, etc.

Unless the context requires otherwise, throughout the specification and claims which follows, the term "comprise" and variations thereof, such as "comprises" and "comprising" are to be construed in an open, inclusive sense, which is as "include, but not limited to".

Reference throughout this specification to "one embodiment", or "an embodiment", or "in another embodiment", or "some embodiments", or "in some embodiments" means that a particular referred feature, structure or characteristic described in connection with the embodiments is included in at least one embodiment. Therefore, the appearance of the phases "in one embodiment", or "in an embodiment", or "in another embodiment", or "in some embodiments" in various places throughout this specification are not necessarily all referring to the same embodiment. Moreover, the particular features, structures or characteristics may be combined in any suitable manner in one or more embodiments.

It should be noted that, as used in this specification and the appended claims, the singular forms "a", "an" and "the" include plural referents unless the content clearly indicate otherwise. Therefore, for example, "mixing an antimicrobial metal with a stainless steel" comprises mixing one antimicrobial metal (such as silver) with one stainless steel (such as a nickel-based stainless steel containing chromium), mixing one antimicrobial metal (such as copper) with several stainless steels (such as a nickel-based stainless steel containing chromium and a cobalt-based stainless steel containing chromium), mixing several antimicrobial metals (such as silver and copper) with one stainless steel (such as a nickel-based stainless steel containing chromium), and mixing several antimicrobial metals (such as silver and copper) with several stainless steels (such as a nickel-based stainless steel containing chromium and a cobalt-based stainless steel containing chromium). It should be also noted that the use of "or" means "and/or", unless specifically stated otherwise.

It should be noted that, all the values of the amount expressing component, reaction conditions and the like, as used in the specification and claims, should be construed as being modified by term "about". Therefore, unless specified to the contrary, all the values of parameters indicated in the specification and appended claims are approximation, and can vary with the required properties as sought in the present application. It is never intended to limit a use of doctrine of equivalents in the scope of claims. Each of values of parameters should be construed according to significant figure and common integral method.

DEFINITION

As used in specification and appended claims, unless specified to the contrary, the following terms have the meaning indicated.

The terms "silver", "element silver", "metal silver", "element metal silver" as used herein refer to the transition metal element ($Ag^0$) with the atomic number of 47 in Group 11 (IB).

The term "silver ion(s)" as used herein refers to silver ion(s) ($Ag^+$) in the oxidation state of +1.

The term "high temperature" as used herein refers to a temperature of about 1000° C. or more, such as more than about 1000° C., 1100° C., 1200° C., 1300° C., 1400° C., 1500° C., 1600° C., 1700° C., 1800° C., 1900° C., 2000° C., 2100° C., 2200° C., 2300° C., 2400° C., 2500° C., 2600° C., 2700° C., 2800° C., 2900° C., and 3000° C.

The term "high pressure" as used herein refers to a pressure more than about 1 bar, such as more than about 1 bar, 1.5 bar, 2.0 bar, 2.5 bar, 3.0 bar, 3.5 bar, 4.0 bar, 4.5 bar, 5.0 bar, 5.5 bar, 6.0 bar, 6.5 bar, 7.0 bar, 7.5 bar, 8.0 bar, 8.5 bar, 9.0 bar, 9.5 bar, and 10.0 bar.

The term "quick(ly)" as used herein refers to a rate of about 120 m/s or more, such as more than about 120 m/s, 130 m/s, 140 m/s, 150 m/s, 160 m/s, 170 m/s, 180 m/s, 190 m/s, 200 m/s, 210 m/s, 220 m/s, 230 m/s, 240 m/s, 250 m/s, 260 m/s, 270 m/s, 280 m/s, 290 m/s, 300 m/s, 310 m/s, 320 m/s, 330 m/s, 340 m/s, 350 m/s, 360 m/s, 370 m/s, 380 m/s, . . . , 980 m/s, 990 m/s, and 1000 m/s.

The term "antimicrobial" or "antimicrobial effects" as used herein refers to the generic terms of inhibiting microbes and killing microbes. The term "inhibiting microbes" or "effects of inhibiting microbes" refers to inhibiting the growth and reproduction of microbes. The term "killing microbes" or "effects of killing microbes" refers to killing trophosomes and propagules of microbes.

The term "antimicrobially effective amount" as used herein refers to an antimicrobial amount which can achieve the desirable antimicrobial effects. Generally, the antimicrobial effects to be achieved may be different according to different antimicrobial requirements. For example, in some embodiments of the present application, an antimicrobially effective amount of silver ions ($Ag^+$) may refer to about 0.0025-30% of the silver ions ($Ag^+$) prepared by the process disclosed in the present application. In some embodiments of the present application, the antimicrobial effects of 99.9% or more can be achieved by applying 0.0025% of silver ions ($Ag^+$) prepared by the process disclosed in the present application on a substrate. In other embodiments, an antimicrobially effective amount of silver ions ($Ag^+$) may refer to about 0.01-20% of the silver ions ($Ag^+$) prepared by the process disclosed in the present application. In other embodiments, an antimicrobial effective amount of silver ions ($Ag^+$) may refer to about 1-10% of the silver ions ($Ag^+$) prepared by the process disclosed in the present application.

The term "metal" as used herein should be understood in a broader sense, i.e., it comprises a single metal, or a mixture of various metals, as well as various alloys, such as an aluminum alloy and a stainless steel.

The term "stainless steel" as used herein refers to the general term of an alloy steel resistant to corrosion, such as air, acid, base and salt. There are various stainless steels. In accordance with the structure of metallographic phase, the stainless steels comprise martensitic, austenitic, ferrite, and duplex type stainless steels and the like. In accordance with the chemical components, the stainless steels comprise two major systems of chromium stainless steel and nickel-chromium stainless steel represented by Cr13 and Cr18Ni8, respectively. Other stainless steels are developed on the basis of the two stainless steels. In accordance with the environmental media during use, the stainless steels comprise stainless steels resistant to nitric acid, sulfuric acid, urea and seawater, and the like. In accordance with the corrosion resistance, the stainless steels comprise anti-pitting stainless steel, stress corrosion resistance stainless steel, abrasion resistance stainless steel, and the like. In accordance with functional characteristics, the stainless steels comprise non-magnetic stainless steel, free cutting stainless steel, high strength stainless steel, low temperature and super low temperature stainless steel, superplastic stainless steel, and the like.

Antimicrobial Mechanism

Silver cations ($Ag^+$) firmly adsorbs and penetrates the cell walls of the bacteria and moulds to damage the electron transport systems, respiratory systems, mass transport systems of the microbes so as to rapidly kill the microbes. After entering the cell bodies, the silver cations ($Ag^+$) can also react with hydroxyls of the bacteria to solidify the proteins of the bacteria and damage the synthetase activity of the bacteria cells, so that the cells lose the ability of schizogamy and die. With the effects of light, the silver ions ($Ag^+$) in oxidation state becomes catalytic activity centers again, to activate oxygen in water and air to produce OH radical groups and active oxygen ions having quite strong oxidation ability, so that the fertility of the bacteria is damaged in a short time to and the bacteria will die. When the bacterial bodies lose activity, the silver ions ($Ag^+$) will dissociate from the bacterial bodies again, so as to repeat sterilization.

Antimicrobial Performance Test Method and Antimicrobial Effects

Antimicrobial Effects

The antimicrobial effects of a product processed with an antimicrobial method can be obtained by the value of antimicrobial activity. The value should not be less than 99%.

Antimicrobial Performance Test Method (I)

The test method for plastic products is used. The test method is suitable for products such as plastic products, metal products and ceramic products except for fiber products.

1. Bacteria Used in Tests (1) *Escherichia coli*

(2) *Staphylococcus aureus*

Table 1 shows the representative bacterial stains, the stains deposit numbers and the stains depository institutions.

TABLE 1

Bacterial Stains Used in Tests

| Bacterial Species | Stains Deposit Nos. | Stains Depository Institutions |
|---|---|---|
| *Escherichia coli* | ATCC 8739 | American Type Culture Collection |
| *Staphylococcus aureus* | ATCC 6538P | American Type Culture Collection |

2. Reagents, Materials, Apparatuses and Devices

| | |
|---|---|
| Alcohol | Microbial grade |
| Beef extract | Microbial grade |
| Peptone | Microbial grade |
| Sodium chloride (NaCl) | Microbial grade |
| Purified water | Microbial grade |
| Agar culture medium | Microbial grade |
| Yeast extract | Microbial grade |
| Glucose | Microbial grade |
| Casein peptone | Microbial grade |
| Soybean peptone | Microbial grade |
| Lecithin | Microbial grade |

| | |
|---|---|
| Nonionic surfactant-tweenum 80 | Microbial grade |
| Potassium dihydrogen phosphate ($KH_2PO_4$) | Microbial grade |
| Dipotassium hydrogen phosphate ($K_2HPO_4$) | Microbial grade |
| Sodium hydroxide (NaOH) | Microbial grade |
| Hydrochloric acid (HCl) | Microbial grade |
| Cotton plug* | OME cotton |
| Platinum inoculating ring | With a ring of about 4 mm on the top |
| Dry heat Sterilizer | Microbial grade |
| Pressure stream sterilizer | Microbial grade |
| Security console | Microbial grade |
| Clean workbench | Microbial grade |
| Straw | Microbial grade |
| Constant temperature incubator | Microbial grade |
| Culture dish | Microbial grade |
| Stomacher | Microbial grade |
| Film | Microbial grade |

*The silicone, metal or morton plug can be used as well

3. Sterilization Method (1) Dry Heat Sterilization

Articles needed to be sterilized are placed in a dry heat sterilizer at a temperature of 160-180° C. and kept 30-60 minutes. Note that after dry heat sterilization, the related devices cannot be used if the cotton plug or package is wet.

(2) High Pressure Stream Sterilization

Water is added into a pressure stream sterilizer. Articles needed to be sterilized are placed in the metal net basket on the metal grid of the pressure stream sterilizer. Then the pressure stream sterilizer is tightly capped. The articles are heated for 15-20 minutes under the pressure of 103000 MPa at the temperature of 121° C. After the heating is finished, the pressure stream sterilizer is naturally cooled below 100° C. The exhaust valve is opened to exhaust the gas, and then the cap is opened. The sterilized articles are taken out. If necessary, the pressure stream sterilizer can be cooled on a clean workbench. The pressure stream sterilizer should keep clean and avoid contaminating cultures or reagents during the process. If necessary, the pot can be washed with neutral detergents, and flushed with sufficient water.

(3) Flame Sterilization

The reagent is put in flame of air or alcohol for sterilization. When a platinum ring is used, it is heated until red. When a test tube is used, it is contacted with flame for 2-3 seconds.

(4) Apparatus Sterilization

A basic or neutral detergent is used to wash glass wares such as test tubes or beakers. The glass wares are then fully washed with water and dried. The glass wares can be used after being sterilized in a dry heat sterilizer or a high pressure stream sterilizer.

4. Bacteria Culture Medium

The following bacteria culture media are used. Commercially available bacteria culture media which has the same composition can also be used.

(1) Nutrient Broth (NB)

5.0 g beef extract, 10.0 g peptone and 5.0 g sodium chloride are added to 1000 mL purified water or deionized water. The mixture is placed in a flask to mix and dissolve. 0.1 mol/L NaOH solution or hydrochloric acid solution is used to adjust pH to 7.0-7.2 (25° C.). The resultant solution is then sterilized with a high pressure stream sterilizer for 30 minutes at 121° C. If not used immediately after preparation, the solution should be preserved at 5-10° C. for less than one month.

(2) Nutrient Agar Culture Medium (NA)

5.0 g beef extract, 10.0 g peptone, 5.0 g sodium chloride and 15.0 g agar are added to 1000 mL purified water or deionized water. The mixture is placed in a flask to mix and then is heated in a boiling bath to sufficiently dissolve. 0.1 mol/L NaOH solution or hydrochloric acid solution is used to adjust pH to 7.0-7.2 (25° C.). The resultant solution is then sterilized with a high pressure stream sterilizer for 30 minutes at 121° C. If not used immediately after preparation, the solution should be preserved at 5-10° C. for less than one month.

(3) Standard Agar Culture Medium 2.5 g Yeast extract, 5.0 g peptone, 1.0 g glucose and 15.0 g agar are added to 1000 mL purified water or deionized water. The mixture is placed in a flask to mix and then is heated in a boiling bath to sufficiently dissolve. 0.1 mol/L NaOH solution or hydrochloric acid solution is used to adjust pH to 7.0-7.2 (25° C.). The resultant solution is then sterilized with a high pressure stream sterilizer for 30 minutes at 121° C. If not used immediately after preparation, the solution should be preserved at 5-10° C. for less than one month.

(4) Sloped Culture Medium 6-10 mL nutrient agar culture (NA) which is melted after heating is poured into a test tube. A high pressure stream sterilizer is used to sterilize the nutrient agar culture and the tube for 30 minutes at 121° C. After sterilization, the test tube is placed on a clean workbench by inclining 15° and then the nutrient agar culture solidifies. If not used immediately after preparation, the solution should be preserved at 5-10° C. for less than one month.

(5) SCDLP Broth Culture Medium 17.0 g casein peptone, 3.0 g soybean peptone, 5.0 g sodium chloride, 2.5 g potassium hydrogen phosphate, 2.5 g glucose and 10.0 g lecithin are added to 1000 mL purified water or deionized water. The mixture is placed in a flask to mix and sufficiently dissolve. 7.0 g nonionic surfactant is added. 0.1 mol/L NaOH solution or hydrochloric acid solution is used to adjust pH to 6.8-7.2 (25° C.). When the culture medium is used, the culture medium is added in a test tube or an erlenmeyer flask. A high pressure stream sterilizer is used to sterilize the culture medium for 30 minutes at 121° C. If not used immediately after preparation, the solution should be preserved at 5-10° C. for less than one month.

(6) Phosphoric Acid Buffer

To a flask is added 34.0 g potassium dihydrogen phosphate. 500 mL purified water or deionized water is added to the flask to sufficiently dissolve potassium dihydrogen phosphate. 0.1 mol/L NaOH solution is used to adjust pH to 6.8-7.2 (25° C.). Purified water or deionized water is then added up to 1000 mL. When the solution is used, the solution is added in test tubes or erlenmeyer flasks, and sterilized with high pressure stream sterilizer for 30 minutes at 121° C. The phosphoric acid buffer which is preserved for one or more months after preparation can not be used.

(7) Phosphoric Acid Buffering Physiological Saline

Physiological saline (comprising 0.85% sodium chloride) is used to dilute the above phosphoric acid buffer (800 times dilution). When phosphoric acid buffering physiological saline is used, it is added in a test tube or an erlenmeyer flask. A high pressure stream sterilizer is used to sterilize phosphoric acid buffering physiological saline for 30 minutes at 121° C. The phosphoric acid buffer which is preserved for one or more months after preparation can not be used.

5. Preservation of Bacteria

The transfer of bacteria should be conducted sterilely. The platinum inoculating ring sterilized by flame is used to scrape a ring of preserved bacteria, and then streak-inoculated to a sloped culture. After culturing for 24-48 hours at 37° C.±1° C., the bacteria are preserved at 5-10° C. The transfer should be conducted once again within a month. However, the generation number of the switch is limited within 10 generations and the bacteria switch cultured is preserved for less than one month.

6. Test Steps (1) Pre-Culturing Test Bacteria

The above preserved stains are inoculated to a sloped culture with a platinum inoculating ring. The stains are cultured for 16-24 hours at 35° C.±1° C., and then transferred again, and cultured for 16-20 hours.

(2) Preparing Test Pieces

A square piece with 50 mm±2 mm (the thickness is less than 10 mm) is cut from the flat portion of a product as a test piece with a standard size. Six crude test pieces and three antimicrobial test pieces are prepared. Of the six crude test pieces, the viable counts of three pieces are immediately measured after inoculating, while the viable counts of the other three pieces are measured after inoculating for 24 hours.

(3) Washing of Test Pieces

The above test pieces are slightly wiped two to three times with absorbent cottons stained with alcohol and then dried sufficiently. If such treatment affects the test results, other suitable methods can be used to clean the test pieces. Non-cleaned test pieces can be used.

(4) Preparing Test Bacteria Solutions

The above broth culture (NB) is diluted 500 times with purified water. 0.1 mol/L of NaOH solution or hydrochloric acid solution is used to adjust pH to 6.8-7.2 (25° C.). The 1/500 NB inoculating solution is prepared by high pressure stream sterilization. One inoculating ring of the above pre-cultured bacteria is taken and dissolved in 1/500 NB inoculating solution. The resultant solution is diluted to $2.5 \times 10^3 - 10 \times 10^3$/mL bacterial counts. If not used immediately, the prepared bacteria solution should be preserved at 0° C. and used within 4 hours.

(5) Inoculating

Figure 3:
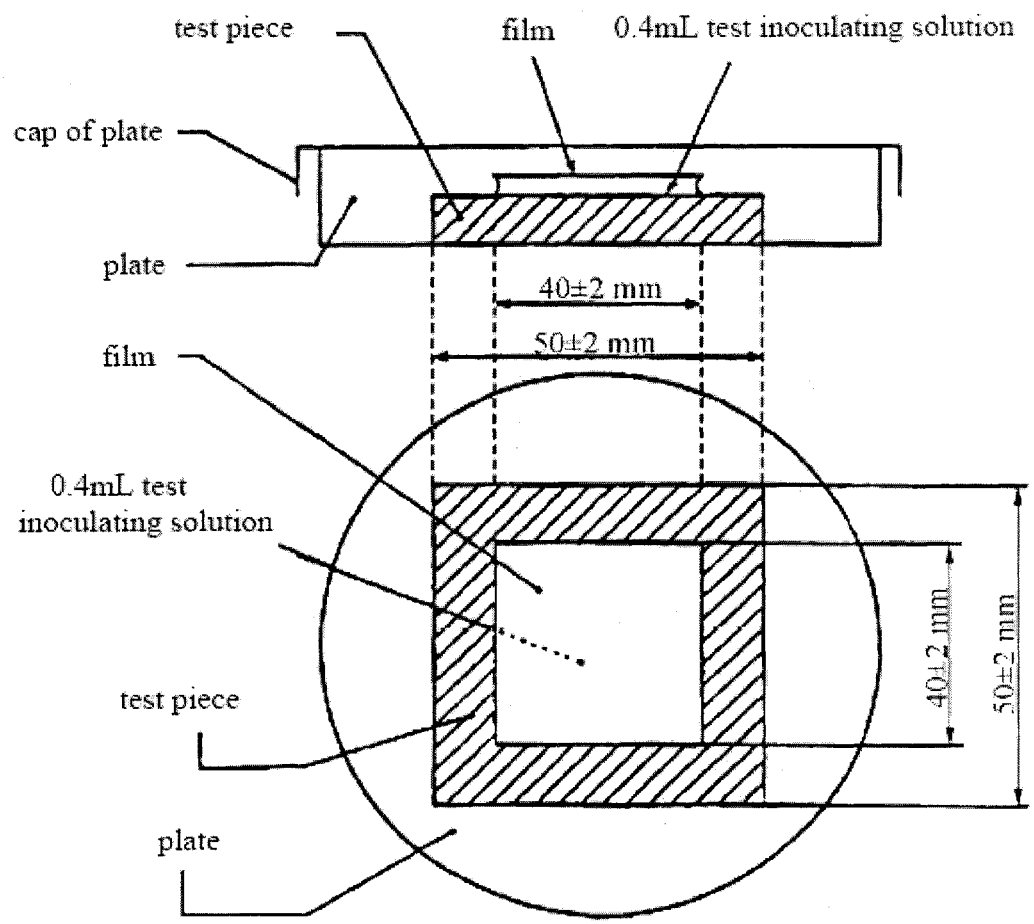
FIG. 3 shows a test piece which is inoculated with bacteria solutions and coated with a film placed on a plate.

The washed test pieces are placed on sterilized plates, respectively. The test surface is placed upwards. 0.4 mL test bacteria solution is accurately taken with a pipette and dropped on each test piece in a plate. The test piece is covered with film. The film is pressed carefully such that the test bacteria solution spreads. It should be noted that the inoculating solution shall not overflow from the outer edge of the film. Finally, a cap is put on the plate (see FIG. 3).

It should be noted that the test surface is the surface of the antimicrobial product. The standard size of the film should be a square with 40 mm±2 mm.

(6) Culturing

The plates with the test pieces inoculated with the test bacteria solutions (three crude test pieces and three antimicrobial product test pieces) are cultured for 24±1 hours at 35° C.±1° C. under the relative humidity of not less than 90%.

(7) Eluting a) Test pieces inoculated with test bacteria solutions

After inoculating the three crude test pieces, the cover films and test pieces are immediately placed in a stomacher sack with tweezers. 10 mL SCDLP broth culture fluid is added with a pipette. The test pieces and cover films in the sack are rubbed with hand for eluting. The viable counts in the eluate are calculated.

b) Cultured Test Pieces

The above cultured test pieces are eluted in the same manner as that for the crude test pieces. The viable counts in the eluate are immediately calculated.

(8) Plate Viable Bacteria Count Method 1 mL the above eluate is accurately drew with a pipette and put into a test tube containing 9.0 mL physiological saline phosphoric acid buffer to sufficiently mix. Then 1 mL the resultant solution is drew from the test tube with a new pipette and put into another test tube containing 9.0 mL physiological saline phosphoric acid buffer to sufficiently mix. The procedure is repeated to conduct a series of 10-fold increasing dilutions. 1 mL eluate and each dilution are added into two sterilized plates, respectively. 15-20 mL standard agar culture medium which is heated to 46-48° C. is placed on each plate to sufficiently mix. The plate is covered with a cap and placed at the ambient temperature. After the culture medium solidifies, the plate is turned over and cultured for 40-48 hours at 35° C.±1° C. After culturing, the number of the plates in which the dilution has 30-300 bacterial counts is calculated. If the bacterial counts on the plate with 1 mL eluate are less than 30, the bacterial counts of the plate are calculated. If no bacterial counts are on the plate, it is recorded as "<1".

7. Calculation of Viable Counts

Viable counts are calculated with the bacterial counts according to the following formula:

$$N = C \times D \times V$$

wherein,

N: viable counts (each test piece)

C: bacterial counts (the mean value of the bacterial counts of the two plates)

D: dilution rate (the rate by which the dilution is made up to the plate)

V: volume (mL) of the SCDLP broth culture medium used in elution

The viable counts are recorded with two significant digits after rounding up or down the third significant digit. If the bacterial counts are "<1", the viable counts therefrom are recorded as "<10" (under the condition of 10 mL) After the mean value of the viable counts is calculated, the arithmetic mean value of viable counts in each of the three test pieces is calculated and recorded with two significant digits after rounding up or down the third significant digit. If the mean value of the viable counts is "<10", the mean value of the viable counts can be recorded as 10.

8. Test Results (1) Judging Conditions for Test Establishment

If the following three conditions are met, the test is determined to be valid. Unless all the conditions are met, the test will be determined to be invalid and shall be carried out again.

a) The directly calculated logarithm value of viable counts obtained from the crude test piece after inoculating should meet:

$$(L_{max} - L_{min})/L_{mv} \leq 0.2$$

wherein, $L_{max}$: maximum logarithm value of viable counts $L_{min}$: minimum logarithm value of viable counts $L_{mv}$: logarithm value of the mean viable counts b) The directly calculated logarithm value of viable count obtained from the crude test piece after inoculating should be in the range of $1.0 \times 10^5 - 4.0 \times 10^5$ cfu/piece.

c) The viable counts of all the three test pieces obtained from the crude test pieces after culturing for 24 hours should not be less than $1.0 \times 10^3$ cfu/piece. However, when cover films are used to cover the crude test pieces, the viable counts of all the three test pieces after placing for 24 hours should not be less than $1.0 \times 10^4$ cfu/piece.

(2) If the test is established, the antimicrobial rate is calculated with the following formula, in which the value has two significant digits after rounding up or down the third significant digit:

$$R(\%) = (B-S)/B \times 100$$

wherein,
R: antimicrobial rate (%)
B: mean recovery viable counts of crude test pieces (cfu/piece)
S: mean recovery viable counts of antimicrobial product test pieces (cfu/piece)

Alternatively, if the test is established, the value of the antimicrobial activity is calculated with the following formula, in which the value has one significant decimal digit after rounding up or down the second significant decimal digit:

$$R = \log(B/A) - \log(C/A) = \log(B/C)$$

wherein,
R: antimicrobial activity cellular counts
A: mean value of viable cellular counts directly obtained from inoculated crude test pieces
B: mean value of viable cellular counts obtained from inoculated crude test pieces after standing for 24 hours
C: mean value of viable cellular counts obtained from inoculated antimicrobial proceed test pieces after standing for 24 hours Antimicrobial Performance Test Method (II)
The test method for ceramic products is used.
1. Bacteria Used in Tests
(1) *Escherichia coli*
(2) *Staphylococcus aureus*
Table 2 shows the representative bacterial stains, the stains deposit numbers and the stains depository institutions.

TABLE 2

Bacterial Stains Used in Tests

| Bacterial Species | Stains Deposit Nos. | Stains Depository Institutions |
|---|---|---|
| *Escherichia coli* | ATCC 25922 | American Type Culture Collection |
| *Staphylococcus aureus* | ATCC 6538 | American Type Culture Collection |

2. Reagents, Materials, Apparatuses and Devices

| | |
|---|---|
| Alcohol | Microbial grade |
| Beef powder | Microbial grade |
| Peptone | Microbial grade |
| Sodium chloride (NaCl) | Microbial grade |
| Purified water | Microbial grade |
| Agar powder | Microbial grade |
| Yeast extract powder | Microbial grade |
| Sodium dihydrogen phosphate (NaH$_2$PO$_4$) | Microbial grade |
| Disodium hydrogen phosphate (Na$_2$HPO$_4$) | Microbial grade |
| Sodium hydroxide (NaOH) | Microbial grade |
| Hydrochloric acid (HCl) | Microbial grade |
| Cotton plug* | OME cotton |
| Platinum inoculating ring | With a ring of about 4 mm on the top |
| Autoclave | Microbial grade |
| Security console | Microbial grade |
| Clean workbench | Microbial grade |
| Straw (1 mL and 10 mL, with accuracy of 0.1) | Microbial grade |
| Constant temperature incubator | Microbial grade |
| Culture dish | Microbial grade |
| Wide-mouth bottle or triangular flask (500 mL) | Microbial grade |
| Film | Microbial grade |
| L-bar | Microbial grade |
| Bacteria standard turbidimetric tube | Microbial grade |

*The silicone, metal or morton plug can be used as well

3. Culture Medium and Reagents
(1) Nutrient Agar Culture Medium
Nutrient agar triangular flask, nutrient agar medium tube slope (agar content of 1.2%), formulation of nutrient agar culture medium (1000 mL) and process for preparing the same are as follows.

| | | | |
|---|---|---|---|
| Agar powder | 12 g | Peptone | 17.5 g |
| Yeast extract powder | 3 g | NaCl | 5.5 g |
| Beaf powder | 6 g | Distilled water | 1000 mL |

Each component except for agar is dissolved in distilled water. The pH of the resultant solution is adjusted 7.4 with 0.1 M NaOH. The agar is added into the solution. The solution is divided into several flasks. The flasks are sealed and the solution is sterilized for 15 minutes in an autoclave at the pressure of 103 kPa.

(2) Diluent Solution
85% physiological saline: 8.5 g of NaCl is added and dissolved in 1000 mL of distilled water. The resultant solution is filtered and divided into several flasks. Then the flasks are sealed and the solution is sterilized for 15 minutes in an autoclave at the pressure of 103 kPa.

Phosphoric acid buffer:
Solution A: 0.2 M Na$_2$HPO$_4$
Solution B: 0.2 M NaH$_2$PO$_4$.
(72 mL A+28 mL B) mixture+5 g NaCl+1000 mL distilled water The pH of the solution is adjusted to 7.0 with 0.1 M NaOH. The three triangular flasks are filled with 100 mL of buffer and sealed. The solution is sterilized for 15 minutes in an autoclave at the pressure of 103 kPa.

(3) Test Samples
Six test pieces are used according to the following procedures in tests for two strains. The test pieces are cleaned and sterilized for further use.

The test for antimicrobial effects is conducted according to single sampling plan. The test samples should be six samples randomly taken from one batch products provided for the test. Three samples are used in the test and the other three samples are stored for further use. Two test pieces are cut from each of the three samples in the test with the desired size for assay (50 mm×50 mm) and used in the tests for two technical indicators.

4. Operation Steps
(1) Test Procedures

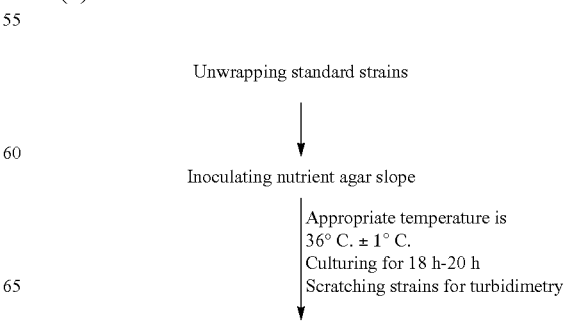

-continued

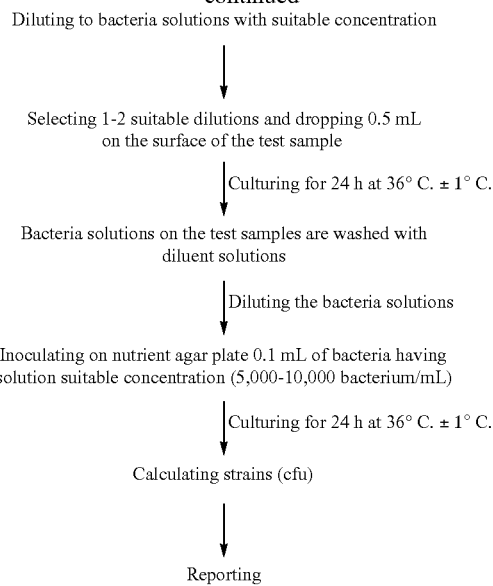

(2) Operation Process

The standard strains are unwrapped. After the tip of the lyophilized strains is heated on flame in a sterile operation, one drop of sterilized physiological saline is dropped with sterilized straw such that the tip appears cracks. The tip is put in eight-layer sterilized gauze and then gently broken off. After the strains are added and dissolved in about 0.1 mL of physiological saline, the strains are inoculated with 3-4 nutrient agar slopes in tubes. The strains are placed in incubator at 36° C.±1° C. and cultured for 18-20 hr, which is referred to as one generation. The resultant strains are stored at 2° C.-8° C. for further use.

The one generation strains are directly inoculated with nutrient agar slope and cultured for 18-20 hr at 36° C.±1° C. The continuously generated third generation is used as strains in the test. If other bacteria are observed in the strains, the strains cannot be used.

Preparation of bacteria solution: the strains are scratched off and diluted to the concentration identical to that of bacteria standard turbidimetric tube, i.e. $5 \times 10^8$ bacterium/ mL.

After the above bacteria solution is diluted to $1.0 \times 10^8$ bacterium/mL, a 10-fold serial dilution is carried out to obtain bacteria solutions with different concentrations of $10^{-1}$-$10^{-6}$.

0.1 mL of the above bacteria solution with dilution of $10^{-6}$ (i.e. 1000 bacterium/mL) is taken and directly inoculated on nutrient agar plate (culturing for 24 h at 36° C.±1° C. and the plate does not contain other bacteria). Three plates in total are cultured for 24 h at 36° C.±1° C. The bacterial count is a bacterial count at 0 h.

0.5 mL of bacteria solution with dilution of $10^{-3}$ (i.e. 1,000,000 bacterium/mL) is taken and separately inoculated on the surface of the test piece of 50 mm×50 mm, then the bacteria solution is flattened. The surface of the test piece is covered with preservative film to maintain the humidity of 90% or more so that the bacteria solution on the surface of the test piece will not dry after 24 h. The bacteria solution is placed in an incubator for 24 h at 36° C.±1° C.

Preparation of bacteria sample at contact time of "0": the test piece is taken immediately after being inoculated. he bacteria solution on the test piece is sufficiently washed with diluent solution. After homogeneously mixing, the resultant solution is diluted by 10-fold increase at a ratio of 1:10. Then the solution is placed and cultured for 24 h in an incubator at 36° C.±1° C.

A test piece after culturing for 24 h is used. 9.5 mL of physiological saline is used to separately wash the bacteria solutions on the test pieces and preservative films into a sterilized plate. The solutions are mixed homogeneously and then diluted to 5000-10000 bacterium/mL.

1-2 appropriate concentrations of the bacteria solution are selected from the range of 5000-10000 bacterium/mL. 0.1 mL of the bacteria solution with each appropriate concentration is calculated for bacterial counts (cfu). The bacteria solution with each dilution is inoculated with three nutrient agar plates. The results are obtained after the bacteria solution is cultured for 24 h at 36° C.±1° C.

5. Calculation of Bacterial Counts (cfu)

(1) Selection of the Bacterial Counts on the Plate

A plate with bacterial counts of 30-300 is selected as a determination standard for the total bacterial counts. Three plates are used for one dilution. The mean value of the bacterial counts in the three plates should be used. If one plate has a larger flake of bacterial colonies, the plate is not suitable to use. A plate having no flake of bacterial colony should be used as bacterial counts for this dilution. If the contribution of the flakes of the bacterial colonies is not more than a half of the plate, while the other half plate has a homogeneous contribution of bacterial colonies, the value calculated from a half of the plate is multiplied by 2 so as to represent the bacterial counts of the whole plate.

(2) Bacterial Colony Count Method

The calculation for plate bacterial counts (cfu) can be observed by naked eyes, if necessary, can be examined with magnifier to avoid omission. The bacterial counts (cfu) in each plate at each dilution are recorded to calculate the average bacterial counts (cfu) of the three plates.

6. Calculation Results $$R(\%)=(B-A)/B \times 100$$

wherein,

R: antimicrobial effects (%)

A: bacterial counts on the test piece after culturing for 24 h

B: bacterial counts on the test piece at contact time of "0"

Specific Embodiments

In one aspect, the present application is directed to a process for preparing silver ions ($Ag^+$), comprising treating element metal silver ($Ag^0$) under high temperature and high pressure, and quickly cooling to directly obtain the silver ions ($Ag^+$).

In some embodiments, a process for preparing silver ions ($Ag^+$) comprises treating element metal silver ($Ag^0$) with burning under high temperature and high pressure, and quickly cooling to directly obtain the silver ions ($Ag^+$).

Exemplary high temperature that can be used in the process for preparing silver ions ($Ag^+$) of the present application is more than about 1000° C., 1100° C., 1200° C., 1300° C., 1400° C., 1500° C., 1600° C., 1700° C., 1800° C., 1900° C., 2000° C., 2100° C., 2200° C., 2300° C., 2400° C., 2500° C., 2600° C., 2700° C., 2800° C., 2900° C., or 3000° C.

Exemplary high pressure that can be used in the process for preparing silver ions ($Ag^+$) of the present application is more than about 1 bar, 1.5 bar, 2.0 bar, 2.5 bar, 3.0 bar, 3.5 bar, 4.0 bar, 4.5 bar, 5.0 bar, 5.5 bar, 6.0 bar, 6.5 bar, 7.0 bar, 7.5 bar, 8.0 bar, 8.5 bar, 9.0 bar, 9.5 bar, or 10.0 bar.

In some embodiments, a process for preparing silver ions ($Ag^+$) comprises treating element metal silvers ($Ag^0$) under temperature of about 1000° C. or more and high pressure, and quickly cooling to directly obtain the silver ions ($Ag^+$).

In some embodiments, a process for preparing silver ions ($Ag^+$) comprises treating element metal silver ($Ag^0$) under high temperature and pressure of more than about 1 bar, and quickly cooling to directly obtain the silver ions ($Ag^+$).

In some preferred embodiments, a process for preparing silver ions ($Ag^+$) comprises treating element metal silver ($Ag^0$) under temperature of about 1000° C. or more and pressure of more than about 1 bar, and quickly cooling to directly obtain the silver ions ($Ag^+$).

In some embodiments, a process for preparing silver ions ($Ag^+$) comprises treating element metal silver ($Ag^0$) with burning under high temperature and high pressure, and quickly cooling with a cooling rate of about 120 m/s or more, to directly obtain the silver ions ($Ag^+$).

Exemplary cooling rate that can be used in the process for preparing silver ions ($Ag^+$) of the present application is more than about 120 m/s, 130 m/s, 140 m/s, 150 m/s, 160 m/s, 170 m/s, 180 m/s, 190 m/s, 200 m/s, 210 m/s, 220 m/s, 230 m/s, 240 m/s, 250 m/s, 260 m/s, 270 m/s, 280 m/s, 290 m/s, 300 m/s, 310 m/s, 320 m/s, 330 m/s, 340 m/s, 350 m/s, 360 m/s, 370 m/s, 380 m/s, . . . , 980 m/s, 990 m/s, or 1000 m/s.

In some embodiments, a process for preparing silver ions ($Ag^+$) comprises treating element metal silver ($Ag^0$) under temperature of about 1000° C. or more and high pressure, and quickly cooling with a cooling rate of about 120 m/s or more, to directly obtain the silver ions ($Ag^+$).

In some embodiments, a process for preparing silver ions ($Ag^+$) comprises treating element metal silver ($Ag^0$) under high temperature and pressure of more than about 1 bar, and quickly cooling with a cooling rate of about 120 m/s or more, to directly obtain the silver ions ($Ag^+$).

In some preferred embodiments, a process for preparing silver ions ($Ag^+$) comprises treating element metal silver ($Ag^0$) under temperature of about 1000° C. or more and pressure of more than about 1 bar, and quickly cooling with a cooling rate of about 120 m/s or more, to directly obtain the silver ions ($Ag^+$).

In some embodiments, a process for preparing silver ions ($Ag^+$) comprises treating element metal silver ($Ag^0$) with burning under high temperature and high pressure, and quickly cooling to a temperature of about 100° C. or less, to directly obtain the silver ions ($Ag^+$).

Exemplary temperature after cooling that can be used in the process for preparing silver ions ($Ag^+$) of the present application is less than about 100° C., 95° C., 90° C., 85° C., 80° C., 75° C., 70° C., 65° C., 60° C., 55° C., 50° C., 45° C., 40° C., 35° C., 30° C., 25° C., or 20° C.

In some embodiments, a process for preparing silver ions ($Ag^+$) comprises treating element metal silver ($Ag^0$) under temperature of about 1000° C. or more and high pressure, and quickly cooling to a temperature of about 100° C. or less, to directly obtain the silver ions ($Ag^+$).

In some embodiments, a process for preparing silver ions ($Ag^+$) comprises treating element metal silver ($Ag^0$) under high temperature and pressure of more than about 1 bar, and quickly cooling to a temperature of about 100° C. or less, to directly obtain the silver ions ($Ag^+$).

In some preferred embodiments, a process for preparing silver ions ($Ag^+$) comprises treating element metal silver ($Ag^0$) under temperature of about 1000° C. or more and pressure of more than about 1 bar, and quickly cooling to a temperature of about 100° C. or less, to directly obtain the silver ions ($Ag^+$).

In some more preferred embodiments, a process for preparing silver ions ($Ag^+$) comprises treating element metal silver ($Ag^0$) under temperature of about 1000° C. or more and pressure of more than about 1 bar, and quickly cooling with a cooling rate of about 120 m/s or more to a temperature of about 100° C. or less, to directly obtain the silver ions ($Ag^+$).

In some embodiments, a process for preparing silver ions ($Ag^+$) comprises treating element metal silver ($Ag^0$) with burning under high temperature and high pressure in a combustion chamber, and quickly cooling to directly obtain the silver ions ($Ag^+$).

In some preferred embodiments, a process for preparing silver ions ($Ag^+$) comprises treating element metal silver ($Ag^0$) under temperature of about 1000° C. or more and pressure of more than about 1 bar in a combustion chamber, and quickly cooling to directly obtain the silver ions ($Ag^+$).

In some more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling with a cooling rate of about 120 m/s or more, to directly obtain the silver ions ($Ag^+$).

In some more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling to a temperature of about 100° C. or less, to directly obtain the silver ions ($Ag^+$).

In some even more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling with a cooling rate of about 120 m/s or more to a temperature of about 100° C. or less, to directly obtain the silver ions ($Ag^+$).

In some embodiments, a process for preparing silver ions ($Ag^+$) comprises treating element metal silver ($Ag^0$) with burning under high temperature and high pressure, and quickly cooling in a gathering device to directly obtain the silver ions ($Ag^+$).

In some preferred embodiments, a process for preparing silver ions ($Ag^+$) comprises treating element metal silver ($Ag^0$) under temperature of about 1000° C. or more and pressure of more than about 1 bar, and quickly cooling in a gathering device, to directly obtain the silver ions ($Ag^+$).

In some more preferred embodiments, a process for preparing silver ions ($Ag^+$) comprises treating element metal silver ($Ag^0$) under temperature of about 1000° C. or more and pressure of more than about 1 bar, and quickly cooling with a cooling rate of about 120 m/s or more in a gathering device, to directly obtain the silver ions ($Ag^+$).

In some more preferred embodiments, a process for preparing silver ions ($Ag^+$) comprises treating element metal silver ($Ag^0$) under temperature of about 1000° C. or more and pressure of more than about 1 bar, and quickly cooling to a temperature of about 100° C. or less in a gather device, to directly obtain the silver ions ($Ag^+$).

In some even more preferred embodiments, a process for preparing silver ions ($Ag^+$) comprises treating element metal silver ($Ag^0$) under temperature of about 1000° C. or more and pressure of more than about 1 bar, and quickly cooling with a cooling rate of about 120 m/s or more to a temperature of about 100° C. or less in a gathering device, to directly obtain the silver ions ($Ag^+$).

In some even more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling with a cooling rate of about 120 m/s or more to a temperature of about 100° C. or less in a gathering device, to directly obtain the silver ions ($Ag^+$).

In some embodiments, a process for preparing silver ions ($Ag^+$) comprises treating element metal silver ($Ag^0$) with burning under high temperature and high pressure, and quickly cooling to directly obtain silver ions ($Ag^+$), wherein the time interval between the high temperature and high pressure treatment and the quick cooling is about one millisecond or less.

In some preferred embodiments, a process for preparing silver ions ($Ag^+$) comprises treating element metal silver ($Ag^0$) under temperature of about 1000° C. or more and pressure of more than about 1 bar in a combustion chamber, and quickly cooling in a gathering device, to directly obtain the silver ions ($Ag^+$), wherein the time interval between the treatment in the combustion chamber and the quick cooling in the gathering device is about one millisecond or less.

In some more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling with a cooling rate of about 120 m/s or more in a gathering device, to directly obtain the silver ions ($Ag^+$), wherein the time interval between the treatment in a combustion chamber and the quick cooling in the gathering device is about one millisecond or less.

In some more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling to a temperature of about 100° C. or less in the combustion chamber, to directly obtain the silver ions ($Ag^+$), wherein the time interval between the treatment in the combustion chamber and the quick cooling in a gathering device is about one millisecond or less.

In some even more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling with a cooling rate of about 120 m/s or more to a temperature of about 100° C. or less in a gathering device, to directly obtain the silver ions ($Ag^+$), wherein the time interval between the treatment in the combustion chamber and the quick cooling in the gathering device is about one millisecond or less.

In some embodiments, a process for preparing silver ions ($Ag^+$) comprises treating element metal silver ($Ag^0$) with burning under high temperature and high pressure, and quickly cooling to directly obtain the silver ions ($Ag^+$), wherein the treatment under high temperature and high pressure is carried out with a flamer.

In some preferred embodiments, a process for preparing silver ions ($Ag^+$) comprises treating element metal silver ($Ag^0$) under temperature of about 1000° C. or more and high pressure, and quickly cooling to directly obtain the silver ions ($Ag^+$), wherein the treatment under temperature of about 1000° C. or more and high pressure is carried out with a flamer.

In some preferred embodiments, a process for preparing silver ions ($Ag^+$) comprises treating element metal silver ($Ag^0$) under high temperature and pressure of more than about 1 bar, and quickly cooling to directly obtain the silver ions ($Ag^+$), wherein the treatment under high temperature and pressure of more than about 1 bar is carried out with a flamer.

In some embodiments, a process for preparing silver ions ($Ag^+$) comprises treating element metal silver ($Ag^0$) in the form of powder or wire with burning under high temperature and high pressure, and quickly cooling to directly obtain the silver ions ($Ag^+$).

In some embodiments, a process for preparing silver ions ($Ag^+$) comprises treating element metal silver ($Ag^0$) with burning under high temperature and high pressure, and quickly cooling to directly obtain the silver ions ($Ag^+$) with antimicrobial effects of about 99.98% or more.

In some preferred embodiments, a process for preparing silver ions ($Ag^+$) comprises treating element metal silver ($Ag^0$) under temperature of about 1000° C. or more and pressure of more than about 1 bar in a combustion chamber, and quickly cooling to directly obtain the silver ions ($Ag^+$).

In some more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling with a cooling rate of about 120 m/s or more, to directly obtain the silver ions ($Ag^+$).

In some more preferred embodiments, a process for preparing silver ions ($Ag^+$) comprises treating element metal silver ($Ag^0$) under temperature of about 1000° C. or more and pressure of more than about 1 bar in a combustion chamber, and quickly cooling to a temperature of about 100° C. or less, to directly obtain the silver ions ($Ag^+$).

In some preferred embodiments, a process for preparing silver ions ($Ag^+$) comprises treating element metal silver ($Ag^0$) under temperature of about 1000° C. or more and pressure of more than about 1 bar, and quickly cooling to directly obtain the silver ions ($Ag^+$) with antimicrobial effects of about 99.98% or more.

In some more preferred embodiments, a process for preparing silver ions ($Ag^+$) comprises treating element metal silver ($Ag^0$) under temperature of about 1000° C. or more and pressure of more than about 1 bar, and quickly cooling with a cooling rate of about 120 m/s or more to a temperature of about 100° C. or less, to directly obtain the silver ions ($Ag^+$) with antimicrobial effects of about 99.98% or more.

In some even more preferred embodiments, a process for preparing silver ions ($Ag^+$) comprises treating element metal silver ($Ag^0$) under temperature of about 1000° C. or more and pressure of more than about 1 bar, and quickly cooling with a cooling rate of about 120 m/s or more to a temperature of about 100° C. or less, to directly obtain the silver ions ($Ag^+$) with antimicrobial effects of about 99.98% or more, wherein the time interval between the treatment under temperature of about 1000° C. or more and pressure of more than about 1 bar and the quick cooling is about one millisecond or less.

In some even more preferred embodiments, a process for preparing silver ions ($Ag^+$) comprises treating element metal silver ($Ag^0$) under temperature of about 2200° C. and pressure of about 4 bar, and quickly cooling with a cooling rate of about 340 m/s to a temperature of about 100° C., to directly obtain the silver ions ($Ag^+$) with antimicrobial effects of about 99.98% or more, wherein the time interval between the treatment under temperature of 2200° C. and pressure of about 4 bar and the quick cooling is about one millisecond or less.

In another aspect, the present application is also directed to silver ions (Ag$^+$) directly obtained by treating element metal silver (Ag$^0$) under high temperature and high pressure, and quickly cooling, wherein the antimicrobial effects of the silver ions (Ag$^+$) are about 99.98% or more.

In some embodiments, the silver ions (Ag$^+$) are directly obtained by treating element metal silver (Ag$^0$) under temperature of about 1000° C. or more and high pressure, and quickly cooling.

In some embodiments, the silver ions (Ag$^+$) are directly obtained by treating element metal silver (Ag$^0$) under high temperature and pressure of more than about 1 bar, and quickly cooling.

In some preferred embodiments, the silver ions (Ag$^+$) are directly obtained by treating element metal silver (Ag$^0$) under temperature of about 1000° C. or more and pressure of more than about 1 bar, and quickly cooling.

In some embodiments, the silver ions (Ag$^+$) are directly obtained by treating element metal silver (Ag$^0$) with burning under high temperature and high pressure, and quickly cooling with a cooling rate of about 120 m/s or more.

Exemplary cooling rate that can be used in the process for preparing silver ions (Ag$^+$) of the present application is more than about 120 m/s, 130 m/s, 140 m/s, 150 m/s, 160 m/s, 170 m/s, 180 m/s, 190 m/s, 200 m/s, 210 m/s, 220 m/s, 230 m/s, 240 m/s, 250 m/s, 260 m/s, 270 m/s, 280 m/s, 290 m/s, 300 m/s, 310 m/s, 320 m/s, 330 m/s, 340 m/s, 350 m/s, 360 m/s, 370 m/s, 380 m/s, . . . , 980 m/s, 990 m/s, or 1000 m/s.

In some embodiments, the silver ions (Ag$^+$) are directly obtained by treating element metal silver (Ag$^0$) under temperature of about 1000° C. or more and high pressure, and quickly cooling with a cooling rate of about 120 m/s or more.

In some embodiments, the silver ions (Ag$^+$) are directly obtained by treating element metal silver (Ag$^0$) under high temperature and pressure of more than about 1 bar, and quickly cooling with a cooling rate of about 120 m/s or more.

In some preferred embodiments, the silver ions (Ag$^+$) are directly obtained by treating element metal silver (Ag$^0$) under temperature of about 1000° C. or more and pressure of more than about 1 bar, and quickly cooling with a cooling rate of about 120 m/s or more.

In some embodiments, the silver ions (Ag$^+$) are directly obtained by treating element metal silver (Ag$^0$) with burning under high temperature and high pressure, and quickly cooling to a temperature of about 100° C. or less.

Exemplary temperature after cooling that can be used in the process for preparing silver ions (Ag$^+$) of the present application is less than about 100° C., 95° C., 90° C., 85° C., 80° C., 75° C., 70° C., 65° C., 60° C., 55° C., 50° C., 45° C., 40° C., 35° C., 30° C., 25° C., or 20° C.

In some embodiments, the silver ions (Ag$^+$) are directly obtained by treating element metal silver (Ag$^0$) under temperature of about 1000° C. or more and high pressure, and quickly cooling to a temperature of about 100° C. or less.

In some embodiments, the silver ions (Ag$^+$) are directly obtained by treating element metal silver (Ag$^0$) under high temperature and pressure of more than about 1 bar, and quickly cooling to a temperature of about 100° C. or less.

In some preferred embodiments, the silver ions (Ag$^+$) are directly obtained by treating element metal silver (Ag$^0$) under temperature of about 1000° C. or more and pressure of more than about 1 bar, and quickly cooling to a temperature of about 100° C. or less.

In some more preferred embodiments, the silver ions (Ag$^+$) are directly obtained by treating element metal silver (Ag$^0$) under temperature of about 1000° C. or more and pressure of more than about 1 bar, and quickly cooling with a cooling rate of about 120 m/s or more to a temperature of about 100° C. or less.

In some embodiments, the silver ions (Ag$^+$) are directly obtained by treating element metal silver (Ag$^0$) with burning under high temperature and high pressure in a combustion chamber, and quickly cooling.

In some preferred embodiments, the silver ions (Ag$^+$) are directly obtained by treating element metal silver (Ag$^0$) under temperature of about 1000° C. or more and pressure of more than about 1 bar in a combustion chamber, and quickly cooling.

In some more preferred embodiments, the silver ions (Ag$^+$) are directly obtained by treating element metal silver (Ag$^0$) under temperature of about 1000° C. or more and pressure of more than about 1 bar in a combustion chamber, and quickly cooling with a cooling rate of about 120 m/s or more.

In some more preferred embodiments, the silver ions (Ag$^+$) are directly obtained by treating element metal silver (Ag$^0$) under temperature of about 1000° C. or more and pressure of more than about 1 bar in a combustion chamber, and quickly cooling to a temperature of about 100° C. or less.

In some even more preferred embodiments, the silver ions (Ag$^+$) are directly obtained by treating element metal silver (Ag$^0$) under temperature of about 1000° C. or more and pressure of more than about 1 bar in a combustion chamber, and quickly cooling with a cooling rate of about 120 m/s or more to a temperature of about 100° C. or less.

In some embodiments, the silver ions (Ag$^+$) are directly obtained by treating element metal silver (Ag$^0$) with burning under high temperature and high pressure, and quickly cooling in a gathering device.

In some preferred embodiments, the silver ions (Ag$^+$) are directly obtained by treating element metal silver (Ag$^0$) under temperature of about 1000° C. or more and pressure of more than about 1 bar, and quickly cooling in a gathering device.

In some more preferred embodiments, the silver ions (Ag$^+$) are directly obtained by treating element metal silver (Ag$^0$) under temperature of about 1000° C. or more and pressure of more than about 1 bar, and quickly cooling with a cooling rate of about 120 m/s or more in a gathering device.

In some more preferred embodiments, the silver ions (Ag$^+$) are directly obtained by treating element metal silver (Ag$^0$) under temperature of about 1000° C. or more and pressure of more than about 1 bar, and quickly cooling to a temperature of about 100° C. or less in a gathering device.

In some even more preferred embodiments, the silver ions (Ag$^+$) are directly obtained by treating element metal silver (Ag$^0$) under temperature of about 1000° C. or more and pressure of more than about 1 bar, and quickly cooling with a cooling rate of about 120 m/s or more to a temperature of about 100° C. or less in a gathering device.

In some even more preferred embodiments, the silver ions (Ag$^+$) are directly obtained by treating element metal silver (Ag$^0$) under temperature of about 1000° C. or more and pressure of more than about 1 bar in a combustion chamber, and quickly cooling with a cooling rate of about 120 m/s or more to a temperature of about 100° C. or less in a gathering device.

In some embodiments, the silver ions ($Ag^+$) are directly obtained by treating element metal silver ($Ag^0$) with burning under high temperature and high pressure, and quickly cooling, wherein the time interval between the high temperature and high pressure treatment and the quick cooling is about one millisecond or less.

In some preferred embodiments, the silver ions ($Ag^+$) are directly obtained by treating element metal silver ($Ag^0$) under temperature of about 1000° C. or more and pressure of more than about 1 bar in a combustion chamber, and quickly cooling in a gathering device, wherein the time interval between the treatment in the combustion chamber and the quick cooling in the gathering device is about one millisecond or less.

In some more preferred embodiments, the silver ions ($Ag^+$) are directly obtained by treating element metal silver ($Ag^0$) under temperature of about 1000° C. or more and pressure of more than about 1 bar in a combustion chamber, and quickly cooling with a cooling rate of about 120 m/s or more in a gathering device, wherein the time interval between the treatment in the combustion chamber and the quick cooling in the gathering device is about one millisecond or less.

In some more preferred embodiments, the silver ions ($Ag^+$) are directly obtained by treating element metal silver ($Ag^0$) under temperature of about 1000° C. or more and pressure of more than about 1 bar in a combustion chamber, and quickly cooling to a temperature of about 100° C. or less in the combustion chamber, wherein the time interval between the treatment in the combustion chamber and the quick cooling in the gathering device is about one millisecond or less.

In some even more preferred embodiments, the silver ions ($Ag^+$) are directly obtained by treating element metal silver ($Ag^0$) under temperature of about 1000° C. or more and pressure of more than about 1 bar in a combustion chamber, and quickly cooling with a cooling rate of about 120 m/s or more to a temperature of about 100° C. or less in the gathering device, wherein the time interval between the treatment in the combustion chamber and the quick cooling in the gathering device is about one millisecond or less.

In some embodiments, the silver ions ($Ag^+$) are directly obtained by treating element metal silver ($Ag^0$) with burning under high temperature and high pressure, and quickly cooling, wherein the high temperature and high pressure treatment is carried out with a flamer.

In some preferred embodiments, the silver ions ($Ag^+$) are directly obtained by treating element metal silver ($Ag^0$) under high temperature of 1000° C. or more and high pressure, and quickly cooling, wherein the treatment under high temperature of 1000° C. or more and high pressure is carried out with a flamer.

In some preferred embodiments, the silver ions ($Ag^+$) are directly obtained by treating element metal silver ($Ag^0$) under high temperature and pressure of more than about 1 bar, and quickly cooling, wherein the treatment under high temperature and high pressure of more than about 1 bar is carried out with a flamer.

In some embodiments, the silver ions ($Ag^+$) are directly obtained by treating element metal silver ($Ag^0$) in the form of powder or wire with burning under high temperature and high pressure, and quickly cooling.

In some embodiments, the silver ions ($Ag^+$) are directly obtained by treating element metal silver ($Ag^0$) with burning under high temperature and high pressure, and quickly cooling, wherein the antimicrobial effects of the silver ions are about 99.98% or more.

In some preferred embodiments, the silver ions ($Ag^+$) is are directly obtained by treating element metal silver ($Ag^0$) under temperature of about 1000° C. or more and pressure of more than about 1 bar in a combustion chamber, and quickly cooling.

In some more preferred embodiments, the silver ions ($Ag^+$) is are directly obtained by treating element metal silver ($Ag^0$) under temperature of about 1000° C. or more and pressure of more than about 1 bar in a combustion chamber, and quickly cooling with a cooling rate of about 120 m/s or more.

In some more preferred embodiments, the silver ions ($Ag^+$) is are directly obtained by treating element metal silver ($Ag^0$) under temperature of about 1000° C. or more and pressure of more than about 1 bar in a combustion chamber, and quickly cooling to a temperature of about 100° C. or less.

In some preferred embodiments, the silver ions ($Ag^+$) is are directly obtained by treating element metal silver ($Ag^0$) under temperature of about 1000° C. or more and pressure of more than about 1 bar, and quickly cooling, wherein the antimicrobial effects of the silver ions are about 99.98% or more.

In some more preferred embodiments, the silver ions ($Ag^+$) are directly obtained by treating element metal silver ($Ag^0$) under temperature of about 1000° C. or more and pressure of more than about 1 bar, and quickly cooling with a cooling rate of about 120 m/s or more to a temperature of about 100° C. or less, wherein the antimicrobial effects of the silver ions are about 99.98% or more.

In some even more preferred embodiments, the silver ions ($Ag^+$) are directly obtained by treating element metal silver ($Ag^0$) under temperature of about 1000° C. or more and pressure of more than about 1 bar, and quickly cooling with a cooling rate of about 120 m/s or more to a temperature of 100° C. or less, wherein the antimicrobial effects of the silver ions are about 99.98% or more, and the time interval between the treatment under temperature of 1000° C. or more and pressure of more than about 1 bar and the quick cooling is about one millisecond or less.

In some even more preferred embodiments, the silver ions ($Ag^+$) are directly obtained by treating element metal silver ($Ag^0$) under temperature of about 2200° C. and pressure of about 4 bar, and quickly cooling with a cooling rate of about 340 m/s to a temperature of about 100° C., wherein the antimicrobial effects of the silver ions are about 99.98% or more, and the time interval between the treatment under temperature of about 2200° C. and pressure of about 4 bar and the quick cooling is about one millisecond or less.

The collected metal silver ions ($Ag^+$) can be widely applied in various fields, such as medical appliance, textile cloth industry, leather clothing, cap and gown, pharmacy, shoe, furniture, holder, building, tableware, daily necessities, and the like.

In still another aspect, the present application is directed to a surface coated with silver ions ($Ag^+$) directly obtained by treating element metal silver ($Ag^0$) under high temperature and high pressure, and quickly cooling.

In some embodiments, the surface is coated with silver ions ($Ag^+$) directly obtained by treating element metal silver ($Ag^0$) with burning under high temperature and high pressure, and quickly cooling.

Exemplary high temperature that can be used in the process for preparing silver ions ($Ag^+$) of the present application is more than about 1000° C., 1100° C., 1200° C., 1300° C., 1400° C., 1500° C., 1600° C., 1700° C., 1800° C., 1900° C., 2000° C., 2100° C., 2200° C., 2300° C., 2400° C., 2500° C., 2600° C., 2700° C., 2800° C., 2900° C., or 3000° C.

Exemplary high pressure that can be used in the process for preparing silver ions ($Ag^+$) of the present application is more than about 1 bar, 1.5 bar, 2.0 bar, 2.5 bar, 3.0 bar, 3.5 bar; 4.0 bar, 4.5 bar, 5.0 bar, 5.5 bar, 6.0 bar, 6.5 bar, 7.0 bar, 7.5 bar, 8.0 bar, 8.5 bar, 9.0 bar, 9.5 bar, or 10.0 bar.

In some embodiments, the surface is coated with silver ions ($Ag^+$) directly obtained by treating element metal silver ($Ag^0$) under temperature of about 1000° C. or more and high pressure, and quickly cooling.

In some embodiments, the surface is coated with silver ions ($Ag^+$) directly obtained by treating element metal silver ($Ag^0$) under high temperature and pressure of more than about 1 bar, and quickly cooling.

In some embodiments, the surface is coated with silver ions ($Ag^+$) directly obtained by treating element metal silver ($Ag^0$) under temperature of about 1000° C. or more and pressure of more than about 1 bar, and quickly cooling.

In some embodiments, the surface is coated with silver ions ($Ag^+$) directly obtained by treating element metal silver ($Ag^0$) with burning under high temperature and high pressure, and quickly cooling with cooling rate of about 120 m/s or more.

Exemplary cooling rate that can be used in the process for preparing silver ions ($Ag^+$) of the present application is more than about 120 m/s, 130 m/s, 140 m/s, 150 m/s, 160 m/s, 170 m/s, 180 m/s, 190 m/s, 200 m/s, 210 m/s, 220 m/s, 230 m/s, 240 m/s, 250 m/s, 260 m/s, 270 m/s, 280 m/s, 290 m/s, 300 m/s, 310 m/s, 320 m/s, 330 m/s, 340 m/s, 350 m/s, 360 m/s, 370 m/s, 380 m/s, . . . , 980 m/s, 990 m/s, or 1000 m/s.

In some embodiments, the surface is coated with silver ions ($Ag^+$) directly obtained by treating element metal silver ($Ag^0$) under temperature of about 1000° C. or more and high pressure, and quickly cooling with a cooling rate of about 120 m/s or more.

In some embodiments, the surface is coated with silver ions ($Ag^+$) directly obtained by treating element metal silver ($Ag^0$) under high temperature and pressure of more than about 1 bar, and quickly cooling with a cooling rate of about 120 m/s or more.

In some preferred embodiments, the surface is coated with silver ions ($Ag^+$) directly obtained by treating element metal silver ($Ag^0$) under temperature of about 1000° C. or more and pressure of more than about 1 bar, and quickly cooling with a cooling rate of about 120 m/s or more.

In some embodiments, the surface is coated with silver ions ($Ag^+$) directly obtained by treating element metal silver ($Ag^0$) with burning under high temperature and high pressure, and quickly cooling to a temperature of about 100° C. or less.

Exemplary temperature after cooling that can be used in the process for preparing silver ions ($Ag^+$) of the present application is less than about 100° C., 95° C., 90° C., 85° C., 80° C., 75° C., 70° C., 65° C., 60° C., 55° C., 50° C., 45° C., 40° C., 35° C., 30° C., 25° C., or 20° C.

In some embodiments, the surface is coated with silver ions ($Ag^+$) directly obtained by treating element metal silver ($Ag^0$) under temperature of about 1000° C. or more and high pressure, and quickly cooling to a temperature of 100° C. or less.

In some embodiments, the surface is coated with silver ions ($Ag^+$) directly obtained by treating element metal silver ($Ag^0$) under high temperature and pressure of more than 1 bar, and quickly cooling to a temperature of 100° C. or less.

In some preferred embodiments, the surface is coated with silver ions ($Ag^+$) directly obtained by treating element metal silver ($Ag^0$) under temperature of about 1000° C. or more and pressure of more than about 1 bar, and quickly cooling to a temperature of 100° C. or less.

In some more preferred embodiments, a surface is coated with silver ions ($Ag^+$) directly obtained by treating element metal silver ($Ag^0$) under temperature of about 1000° C. or more and pressure of more than about 1 bar, and quickly cooling with a cooling rate of about 120 m/s or more to a temperature of about 100° C. or less.

In some embodiments, the surface is coated with silver ions ($Ag^+$) directly obtained by treating element metal silver ($Ag^+$) with burning under high temperature and a high pressure in a combustion chamber, and quickly cooling.

In some preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling.

In some more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling with a cooling rate of about 120 m/s or more.

In some more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling to a temperature of 100° C. or less.

In some even more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling with a cooling rate of about 120 m/s or more to a temperature of about 100° C. or less.

In some embodiments, the surface is coated with silver ions ($Ag^+$) directly obtained by treating element metal silver ($Ag^0$) with burning under high temperature and high pressure, and quickly cooling in a gathering device.

In some embodiments, the surface is coated with silver ions ($Ag^+$) directly obtained by treating element metal silver ($Ag^0$) under temperature of about 1000° C. or more and pressure of more than about 1 bar, and quickly cooling in a gathering device.

In some more preferred embodiments, the surface is coated with silver ions ($Ag^+$) directly obtained by treating element metal silver ($Ag^0$) under temperature of about 1000° C. or more and pressure of more than about 1 bar, and quickly cooling with a cooling rate of about 120 m/s or more in a gathering device.

In some more preferred embodiments, the surface is coated with silver ions ($Ag^+$) directly obtained by treating element metal silver ($Ag^0$) under temperature of about 1000° C. or more and pressure of more than about 1 bar, and quickly cooling to a temperature of 100° C. or less in a gathering device.

In some even more preferred embodiments, the surface is coated with silver ions ($Ag^+$) directly obtained by treating element metal silver ($Ag^0$) under temperature of about 1000° C. or more and pressure of more than about 1 bar, and quickly cooling with a cooling rate of about 120 m/s or more to a temperature of about 100° C. or less in a gathering device.

In some even more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling with a cooling rate of about 120 m/s or more to a temperature of about 100° C. or less in a gathering device.

In some embodiments, the surface is coated with silver ions ($Ag^+$) directly obtained by treating element metal silver ($Ag^0$) with burning under high temperature and a high pressure, and quickly cooling, wherein the time interval between the high temperature and a high pressure treatment and the quick cooling is about one millisecond or less.

In some preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling in a gathering device, wherein the time interval between the treatment in the combustion chamber and the quick cooling in the gathering device is about one millisecond or less.

In some more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling with a cooling rate of about 120 m/s or more in a gathering device, wherein the time interval between the treatment in the combustion chamber and the quick cooling in the gathering device is about one millisecond or less.

In some more preferred embodiments, the surface is coated with silver ions ($Ag^+$) directly obtained by treating element metal silver ($Ag^0$) to under temperature of about 1000° C. or more and pressure of more than about 1 bar in a combustion chamber, and quickly cooling to a temperature of about 100° C. or less in the combustion chamber, wherein the time interval between the treatment in the combustion chamber and the quick cooling in a gathering device is about one millisecond or less.

In some even more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling with a cooling rate of about 120 m/s or more to a temperature of about 100° C. or less in a gathering device, wherein the time interval between the treatment in the combustion chamber and the quick cooling in the gathering device is about one millisecond or less.

In some embodiments, the surface is coated with silver ions ($Ag^+$) directly obtained by treating element metal silver ($Ag^0$) with burning under high temperature and high pressure, and quickly cooling, wherein the high temperature and high pressure treatment is carried out with a flamer.

In some preferred embodiments, the surface is coated with silver ions ($Ag^+$) directly obtained by treating element metal silver ($Ag^0$) under temperature of 1000° C. or more and high pressure, and quickly cooling, wherein the treatment under temperature of 1000° C. or more and high pressure is carried out with a flamer.

In some preferred embodiments, the surface is coated with silver ions ($Ag^+$) directly obtained by treating element metal silver ($Ag^0$) under high temperature and pressure of more than about 1 bar, and quickly cooling, wherein the treatment under high temperature and pressure of more than about 1 bar is carried out with a flamer.

In some embodiments, the surface is coated with silver ions ($Ag^+$) directly obtained by treating element metal silver ($Ag^0$) in the form of powder or wire with burning under high temperature and high pressure, and quickly cooling.

In some embodiments, the surface is coated with silver ions ($Ag^+$) directly obtained by treating element metal silver ($Ag^0$) with burning under high temperature and high pressure, and quickly cooling, wherein the antimicrobial effects of the silver ions are about 99.98% or more.

In some embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling.

In some more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling with a cooling rate of about 120 m/s or more.

In some more preferred embodiments, the surface is coated with silver ions ($Ag^+$) directly obtained by treating element metal silver ($Ag^0$) under temperature of about 1000° C. or more and pressure of more than about 1 bar in a combustion chamber, and quickly cooling to a temperature of 100° C. or less.

In some embodiments, the surface is coated with silver ions ($Ag^+$) directly obtained by treating element metal silver ($Ag^0$) under temperature of about 1000° C. or more and pressure of more than about 1 bar, and quickly cooling, wherein the antimicrobial effects of the silver ions are about 99.98% or more.

In some more preferred embodiments, the surface is coated with silver ions ($Ag^+$) directly obtained by treating element metal silver ($Ag^0$) under temperature of about 1000° C. or more and pressure of more than about 1 bar, and quickly cooling with a cooling rate of about 120 m/s or more to a temperature of about 100° C. or less, wherein the antimicrobial effects of the silver ions are about 99.98% or more.

In some even more preferred embodiments, the surface is coated with silver ions ($Ag^+$) directly obtained by treating element metal silver ($Ag^0$) under temperature of about 1000° C. or more and pressure of more than about 1 bar, and quickly cooling with a cooling rate of about 120 m/s or more to a temperature of 100° C. or less, wherein the antimicrobial effects of the silver ions are about 99.98% or more, and the time interval between the treatment under temperature of 1000° C. or more and pressure of more than about 1 bar and the quick cooling is about one millisecond or less.

In some even more preferred embodiments, the surface is coated with silver ions ($Ag^+$) directly obtained by treating element metal silver ($Ag^0$) under temperature of about 2200° C. and pressure of about 4 bar, and quickly cooling with a cooling rate of about 340 m/s to a temperature of about 100° C., wherein the antimicrobial effects of the silver ions are about 99.98% or more, and the time interval between the treatment under temperature of 2200° C. and pressure of about 4 bar and the quick cooling is about one millisecond or less.

In yet another aspect, the present application is directed to a process for preparing an antimicrobial surface, comprising coating silver ions ($Ag^+$) obtained by treating element metal silver (Ag⁰) under high temperature and high pressure and quickly cooling, on a surface to obtain the antimicrobial surface.

In some embodiments, the process for preparing an antimicrobial surface comprises coating silver ions (Ag⁺) obtained by treating element metal silver (Ag⁰) to with burning under high temperature and high pressure and quickly cooling, on a surface to obtain the antimicrobial surface.

In some embodiments, the temperature in the treatment under high temperature and high pressure in the process for preparing an antimicrobial surface is about 1000° C. or more.

In some embodiments, the pressure in the treatment under high temperature and high pressure in the process for preparing an antimicrobial surface is more than about 1 bar.

In some embodiments, a cooling rate in the process for preparing an antimicrobial surface is about 120 m/s or more.

In some embodiments, a temperature after the cooling in the process for preparing an antimicrobial surface is about 100 m/s or less.

In some embodiments, the treatment under high temperature and high pressure in the process for preparing an antimicrobial surface is carried out in a combustion chamber.

In some embodiments, the quick cooling in the process for preparing an antimicrobial surface comprises is carried out in a gathering device.

In some embodiments, a time interval between the treatment under high temperature and high pressure and the quick cooling in the process for preparing an antimicrobial surface comprises is one millisecond or less.

In some embodiments, the treatment under high temperature and high pressure in the process for preparing an antimicrobial surface is carried out with a flamer.

In some embodiments, the element metal silver (Ag⁰) in the process for preparing an antimicrobial surface is in the form of powder or wire.

In some embodiments, antimicrobial effects of silver ions (Ag⁺) in the process for preparing an antimicrobial surface comprises are about 99.98% or more.

In some embodiments, a particle size of silver ions (Ag⁺) in the process for preparing an antimicrobial surface is greater than nanoscale.

In some embodiments, the process for preparing an antimicrobial surface does not require metal oxides.

In some preferred embodiments, the process for preparing an antimicrobial surface comprises coating silver ions (Ag⁺) directly obtained by treating element metal silver (Ag⁰) under temperature of about 1000° C. or more and pressure of more than about 1 bar and quickly cooling, on a surface to obtain the antimicrobial surface.

In some preferred embodiments, the process for preparing an antimicrobial surface comprises coating silver ions (Ag⁺) directly obtained by treating element metal silver (Ag⁰) under temperature of about 1000° C. or more and pressure of more than about 1 bar and quickly cooling with cooling rate of about 120 m/s or more, on a surface to obtain the antimicrobial surface.

In some preferred embodiments, the process for preparing an antimicrobial surface comprises coating silver ions (Ag⁺) directly obtained by treating element metal silver (Ag⁰) under temperature of about 1000° C. or more and pressure of more than about 1 bar, and quickly cooling with cooling rate of about 120 m/s or more to a temperature of about 100° C. or less, on a surface to obtain the antimicrobial surface.

In some more preferred embodiments, the process for preparing an antimicrobial surface comprises coating silver ions (Ag⁺) directly obtained by treating element metal silver (Ag⁰) under temperature of about 1000° C. or more and pressure of more than about 1 bar, and quickly cooling with a cooling rate of about 120 m/s or more to a temperature of 100° C. or less, on a surface to obtain the antimicrobial surface, wherein the time interval between the treatment under temperature of 1000° C. or more and pressure of more than about 1 bar and the quick cooling is about one millisecond or less.

In yet still another aspect, the present application is also directed to an process for inhibiting microbes, comprising applying an antimicrobially effective amount of silver ions (Ag⁺) directly obtained by treating element metal silver (Ag⁰) under high temperature and high pressure and quickly cooling, to a product in need of antimicrobial effects.

Hereafter, detailed illustration will be carried out through the following examples referring to accompanying figures for better understanding of the various aspects and advantages of the present invention. However, it will be appreciated that the following examples are non-limiting and only for illustrating some embodiments of the present invention.

EXAMPLES

Example 1

A suitable amount of powdery element metal silver (Ag⁰) was sent into a conventional flamer (the burning temperature of the flame was 1000° C. and the pressure was 1.0 bar). The directly obtained silver ion (Ag⁺) particles were sent out by flame. The silver ion (Ag⁺) particles arrived in a gathering device at a rate of 120 m/s in one millisecond from the flame. The silver ion (Ag⁺) particles were quickly cooled to 100° C. The resultant silver ion (Ag⁺) particles were collected.

Example 2

A suitable amount of element metal silver (Ag0) in the form of wire was sent into a conventional flamer (the burning temperature of the flame was 1200° C. and the pressure was 1.2 bar). The directly obtained silver ion (Ag⁺) particles were sent out by flame. The silver ion (Ag⁺) particles arrived in a gathering device at a rate of 150 m/s in one millisecond from the flame. The silver ion (Ag⁺) particles were quickly cooled to 90° C. The resultant silver ion (Ag⁺) particles were collected.

Example 3

A suitable amount of powdery element metal silver (Ag⁰) was sent into a conventional flamer (the burning temperature of the flame was 1500° C. and the pressure was 1.5 bar). The directly obtained silver ion (Ag⁺) particles were sent out by flame. The silver ion (Ag⁺) particles arrived in a gathering device at a rate of 200 m/s in one millisecond from the flame. The silver ion (Ag⁺) particles were quickly cooled to 90° C. The resultant silver ion (Ag⁺) particles were collected.

Example 4

A suitable amount of element metal silver (Ag0) in the form of wire was sent into a conventional flamer (the burning temperature of the flame was 1800° C. and the pressure was 1.5 bar). The directly obtained silver ion (Ag⁺) particles were sent out by flame. The silver ion (Ag⁺)

particles arrived in a gathering device at a rate of 300 m/s in one millisecond from the flame. The silver ion (Ag$^+$) particles were quickly cooled to 80° C. The resultant silver ion (Ag$^+$) particles were collected.

Example 5

A suitable amount of powdery element metal silver (Ag$^0$) was sent into a conventional flamer (the burning temperature of the flame was 2000° C. and the pressure was 4.0 bar). The directly obtained silver ion (Ag$^+$) particles were sent out by flame. The silver ion (Ag$^+$) particles arrived in a gathering device at a rate of 340 m/s in one millisecond from the flame. The silver ion (Ag$^+$) particles were quickly cooled to 60° C., The resultant silver ion (Ag$^+$) particles were collected.

Example 6

A suitable amount of powdery element metal silver (Ag0) was sent into a conventional flamer (the burning temperature of the flame was 2200° C. and the pressure was 4.0 bar). The directly obtained silver ion (Ag$^+$) particles were sent out by flame. The silver ion (Ag$^+$) particles arrived in a gathering device at a rate of 360 m/s in one millisecond from the flame. The silver ion (Ag$^+$) particles were quickly cooled to 60° C. The resultant silver ion (Ag$^+$) particles were collected.

Example 7

A suitable amount of element metal silver (Ag$^0$) in the form of wire was sent into a conventional flamer (the burning temperature of the flame was 2200° C. and the pressure was 5.0 bar). The directly obtained silver ion (Ag$^+$) particles were sent out by flame. The silver ion (Ag$^+$) particles arrived in a gathering device at a rate of 360 m/s in one millisecond from the flame. The silver ion (Ag$^+$) particles were quickly cooled to 60° C. The resultant silver ion (Ag$^+$) particles were collected.

Example 8

The antimicrobial performance test method (I) as described in the present application was used to assay the antimicrobial effects of the silver ions (Ag$^+$) obtained in Example 5. The results are shown in Table 3.

TABLE 3

| Names of Tested Bacteria (Stains Deposit Nos.) | Concentrations of bacteria (cfu/mL) | Counts of Recovered Bacteria | | | Logarithmic Values of Antimicrobial Activity |
|---|---|---|---|---|---|
| | | | Contact Time of "0 hr" | Contact Time of "24 hr" | |
| Escherichia coli ATCC 8739 | 5.6 × 10$^5$ | Sample Control | / 1.0 × 10$^5$ | <10 1.5 × 10$^5$ | >4.2 |
| Staphylococcus aureus ATCC 6538P | 5.6 × 10$^5$ | Sample Control | / 1.1 × 10$^5$ | <10 1.5 × 10$^5$ | >4.0 |

As seen from Table 3, the silver ions obtained according to the process for preparing silver ions in the present application have logarithmic values of >4.2 for antimicrobial activity on Escherichia coli, and of >4.0 for antimicrobial activity on Staphylococcus aureus. Therefore, both of the antimicrobial activities meet the standards of antimicrobial activity and efficacy of antimicrobial products in the art (logarithmic value of antimicrobial activity≥2.0).

Example 9

The antimicrobial performance test method (II) as described in the present application was used to assay the antimicrobial effects of the silver ions (Ag$^+$) obtained in Example 6. The results are shown in Table 4.

TABLE 4

| Names of Tested Bacteria (Stains Deposit Nos.) | Counts of Inoculum at "0" hr (cfu/piece) | Counts of Inoculum after 24 hr (cfu/piece) | Antimicrobial effects (%) |
|---|---|---|---|
| Escherichia coli ATCC 25922 | 3.8 × 10$^5$ | <50 | >99.99 |
| Staphylococcus aureus ATCC 6538 | 3.2 × 10$^5$ | <50 | >99.98 |

As seen from Table 4, the silver ions obtained according to the process for preparing silver ions in the present application have antimicrobial effects of >99.99 on Escherichia coli, and antimicrobial effects of >99.98 on Staphylococcus aureus. Therefore, both of the antimicrobial rates meet the standards of antimicrobial activity and efficacy of antimicrobial products in the art (the antimicrobial effects are not less than 99%).

Furthermore, the volumes of the silver ions obtained according to the process for preparing silver ions as described in the present application are quite larger than those at nano scale of silver ions obtained according to electrochemical process. Therefore, the time and intensity of the sustained release of the silver ions obtained according to the process for preparing silver ions as described in the present application are quite longer and stronger than those of silver ions obtained according to a conventional process in the art.

These and other changes can be made in light of the above-detailed description. In general, in the following claims, the terms used should be not construed to be limiting to the specific embodiments disclosed in the specification and claims, but should be construed to include all systems, devices and/or methods that operate in accordance with the claims. Accordingly, the scope of the present invention is not limited by the disclosure, but instead its scope is to be determined entirely by the following claims.

All of the above patents, patent application publications, patent applications, and non-patent publications referred to in this specification are incorporated herein by reference in their entirety.

From the forgoing it will be appreciated, although specific embodiments of the present invention have been described herein for purposes of illustration, various modifications may be made without deviating from the spirit and scope of the present invention. Accordingly, the present application is only limited by the appended claims.

What is claimed is:

1. A process for preparing silver ions (Ag$^+$), comprising:
   using a conventional flamer to directly treat elemental metal silver (Ag$^0$) in the form of powder or wire with burning at a temperature of about 2000-3000° C. and at a pressure of more than about 1 bar;
   sending the obtained silver ion (Ag$^+$) particles out by flame; and
   cooling to a temperature of about 100° C. or less within one millisecond or less to directly obtain the silver ions (Ag$^+$),
   wherein the silver ions (Ag$^+$) move from the flame of the flamer to a gathering device at a rate of about 340-1,000 m/s and wherein the silver ions (Ag$^+$) have antimicrobial effects of about 99.98% or more.

2. The process of claim 1, wherein the burning is carried out in a combustion chamber.

3. The process of claim 1, wherein the cooling is carried out in a gathering device.

4. The process of claim 1, wherein the process does not require metal oxides.

5. The process of claim 1, wherein the cooling step cools the obtained silver ion (Ag$^+$) particles to a temperature of about 80° C. or less within one millisecond or less to directly obtain the silver ions (Ag$^+$).

6. The process of claim 1, wherein the cooling step cools the obtained silver ion (Ag$^+$) particles to a temperature of about 60° C. or less within one millisecond or less to directly obtain the silver ions (Ag$^+$).

* * * * *